(12) United States Patent
Martins et al.

(10) Patent No.: US 9,000,214 B2
(45) Date of Patent: Apr. 7, 2015

(54) PROCESS FOR PURIFYING TEREPHTHALIC ACID USING IONIC LIQUIDS

(71) Applicant: UOP LLC, Des Plaines, IL (US)

(72) Inventors: Susie C. Martins, Carol Stream, IL (US); Kaitlin DeSalvo, Des Plaines, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 61 days.

(21) Appl. No.: 13/911,130

(22) Filed: Jun. 6, 2013

(65) Prior Publication Data

US 2013/0331603 A1 Dec. 12, 2013

Related U.S. Application Data

(60) Provisional application No. 61/657,499, filed on Jun. 8, 2012.

(51) Int. Cl.
*C07C 51/42* (2006.01)
*C07C 51/43* (2006.01)

(52) U.S. Cl.
CPC ................. *C07C 51/42* (2013.01); *C07C 51/43* (2013.01)

(58) Field of Classification Search
None
See application file for complete search history.

(56) References Cited

U.S. PATENT DOCUMENTS

| | | |
|---|---|---|
| 2010/0174111 A1 | 7/2010 | Rogers |
| 2012/0004449 A1 | 1/2012 | Bhattacharyya |
| 2012/0004450 A1 | 1/2012 | Bhattacharyya |
| 2012/0004454 A1 | 1/2012 | Bhattacharyya |
| 2012/0004455 A1 | 1/2012 | Bhattacharyya |

FOREIGN PATENT DOCUMENTS

WO  WO 2008/151034  * 11/2008 .............. C07C 51/42

* cited by examiner

*Primary Examiner* — Yevegeny Valenrod

(57) ABSTRACT

Methods of purifying crude or contaminated terephthalic acid using ionic liquids are described. Crude or contaminated terephthalic acid is contacted with a solvent in the absence of an oxidizing agent to form a purified product having at least 30 wt % less 4-carboxybenzaldehyde compared to the crude or contaminated terephthalic acid. The solvent consists essentially of an ionic liquid, optionally an ionic solid or a material capable of forming an ionic salt, and optionally an aqueous solvent. The ionic liquid is formed in situ from at least one ionic liquid precursor.

19 Claims, 1 Drawing Sheet

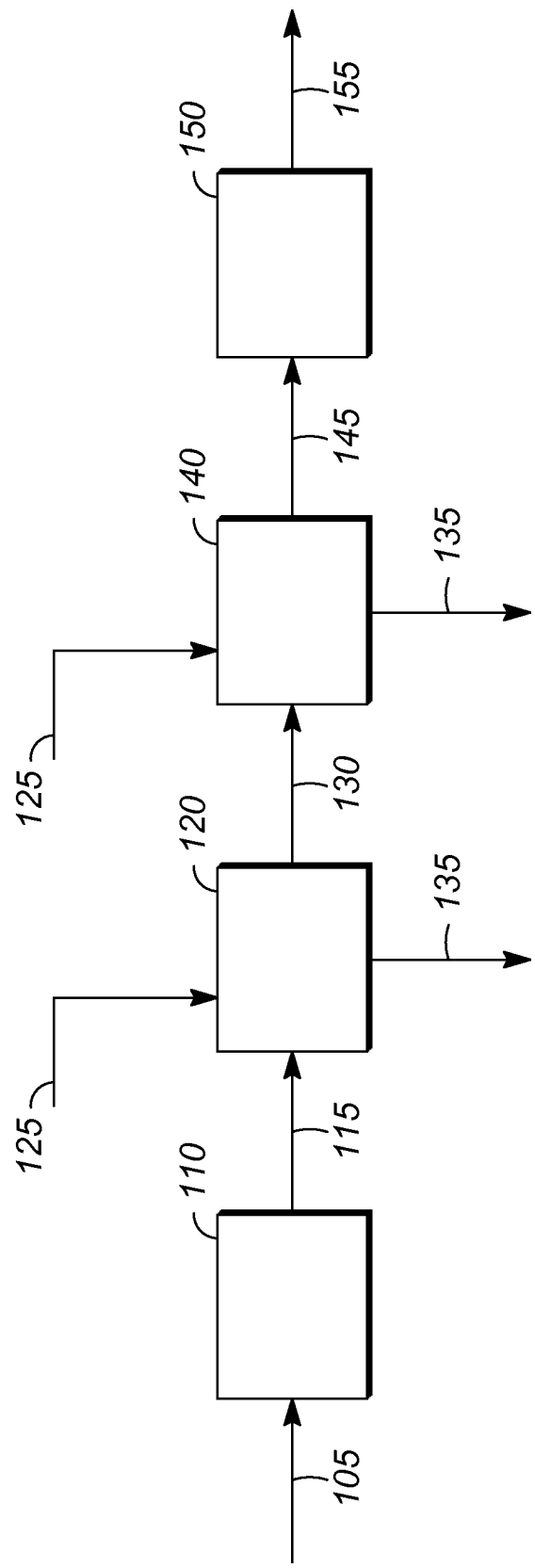

PROCESS FOR PURIFYING TEREPHTHALIC ACID USING IONIC LIQUIDS

CROSS REFERENCE TO RELATED APPLICATION

This application claims benefit of U.S. Application No. 61/657,499 which was filed on Jun. 8, 2012.

FIELD OF THE INVENTION

This invention relates to processes for purifying terephthalic acid. More particularly, the invention relates to processes for purifying crude or contaminated terephthalic acid using ionic liquids.

BACKGROUND OF THE INVENTION

Oxidation of alkyl aromatic compounds, e.g., toluene and xylenes, are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as a reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). The 4-CBA is difficult to remove because it co-crystallizes with terephthalic acid in many existing manufacturing processes. To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. However, the catalytic hydrogenation process requires a significant investment in equipment and is expensive to operate. Often several purification steps are used to obtain the needed purity.

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

SUMMARY OF THE INVENTION

One aspect of the present invention is a process for purifying crude or contaminated terephthalic acid. In one embodiment, the method includes contacting the crude or contaminated terephthalic acid with a solvent in the absence of an oxidizing agent to form a purified product having at least 30 wt % less 4-carboxybenzaldehyde compared to the crude or contaminated terephthalic acid, wherein the solvent consists essentially of an ionic liquid, optionally an ionic solid or a material capable of forming an ionic salt, and optionally an aqueous solvent; and separating the purified product from the solvent.

BRIEF DESCRIPTION OF THE DRAWING

The FIGURE is a schematic of one embodiment of a process of the present invention.

DETAILED DESCRIPTION OF THE INVENTION

The present invention provides a simple purification process which eliminates the need for an expensive catalytic hydrogenation process.

The process involves contacting the crude or contaminated terephthalic acid, (however obtained) with a solvent containing one or more ionic liquids, optionally an ionic solid or a material capable of forming an ionic salt, and optionally an aqueous solvent to produce a product having a lower amount of contaminants than is in the initial crude or contaminated terephthalic acid. No oxidizing agent is present, and no oxidation takes place.

The crude or contaminated terephthalic acid can be a solid, a slurry, or a solid in contact with a saturated solution.

The solvent containing the ionic liquid is at a temperature in the range of about room temperature to about 250° C., or about room temperature to about 200° C., or about 50° C. to about 250° C., or about 50° C. to about 200° C. The crude or contaminated terephthalic acid is contacted with the solvent containing the ionic liquid (and other components, if any) for a period of at least about 15 min, or at least about 1 hr or more. The ionic liquid is then separated from the terephthalic acid using any known solid/liquid separation method. Suitable separation methods include, but are not limited to, filtration, settling, decantation, and centrifugation. Nothing is added to the solvent/crude or contaminated terephthalic acid mixture, and the terephthalic acid is not precipitated. The separation can be batch or continuous. The terephthalic acid is then recovered. It can be washed with water if needed to remove any remaining ionic liquid. The process can be repeated to obtain the desired purity.

The product, after one or more contacting steps, can contain less than about 2500 ppm 4-CBA, or less than about 2000 ppm 4-CBA, or less than about 1500 ppm 4-CBA, or less than about 1000 ppm 4-CBA, or less than about 750 ppm 4-CBA, or less than about 500 ppm 4-CBA, or less than about 250 ppm 4-CBA, or less than about 100 ppm 4-CBA, or less than about 50 ppm 4-CBA, or less than about 25 ppm 4-CBA.

As illustrated in the FIGURE, the feed 105 enters reactor 110 and reacts to form crude or contaminated terephthalic acid 115, from which contaminants, such as 4-CBA, need to be removed. The crude or contaminated terephthalic acid 115 enters a tank 120 where it is contacted with the solvent 125 containing the ionic liquid, optional ionic solid or material capable of forming an ionic salt, and the optional aqueous solvent (collectively ionic liquid). The terephthalic acid 130 is separated from the used ionic liquid 135. The terephthalic acid 130 has a level of contaminants, such as 4-CBA, less than the level of contaminants in the crude or contaminated terephthalic acid 115 entering the tank 120. The terephthalic acid 130 with the reduced level of contaminants can optionally be sent to another tank 140 (or more than one) for additional purification with solvent 125, if needed. The terephthalic acid 145 exiting the second tank 140 has a level of contaminants less than the level in the terephthalic acid 130 entering the tank 140. The terephthalic acid 145 can then be sent to a separation zone 150 to obtain the final terephthalic acid product 155.

The crude or contaminated terephthalic acid can be obtained using any known process for oxidizing alkyl-aromatic compounds, including, but not limited to, those described in U.S. Pat. Nos. 2,833,816; 6,355,835; 7,094,925; 7,985,875; and 7,692,036; and US Publication Nos. 2007/0155985, 2007/0208193, and 2010/0200804 each of which is incorporated herein by reference. Other suitable processes are described in US Publication Nos. 2012/0004448, 2012/0004449, 2012/0004450, 2012/0004451, 2012/0004454, 2012/0004455, and 2012/0004456, each of which is incorporated herein by reference.

The contacting step(s) may be practiced in laboratory scale experiments through full scale commercial operations. The process may be operated in batch, continuous, or semi-continuous mode. The contacting step can take place in various ways.

The solvent includes at least one ionic liquid. Two or more ionic liquids can be used, if desired.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Most ionic liquids are formed from cations that do not contain acidic protons. The synthesis of ionic liquids can generally be split into two parts: formation of the desired cation, and anion exchange to form the desired product. Quaternization of an amine or phosphine, for example, is the initial step in the synthesis of the cation of an ionic liquid. If it is not possible to form the desired anion directly by the quaternization reaction, a further step is required.

There are estimated to be hundreds of thousands of simple ion combinations to make ionic liquids, and an almost endless (1018) number of potential ionic liquid mixtures. This implies that it should be possible to design an ionic liquid with the desired properties to suit a particular application by selecting anions, cations, and mixture concentrations. Ionic liquids can be adjusted or tuned to provide a specific melting point, viscosity, density, hydrophobicity, miscibility, etc. for specific applications. The thermodynamics and reaction kinetics of processes carried out in ionic liquids are different from those in conventional media. This creates new opportunities for catalytic reactions, separations, extractions, combined reaction/separation processes, heat transfer agents, hydraulic fluids, paint additives, electrochemistry applications, as well as many others. Ionic liquids do not emit volatile organic compounds (VOCs), providing a basis for clean manufacturing, e.g., "green chemistry."

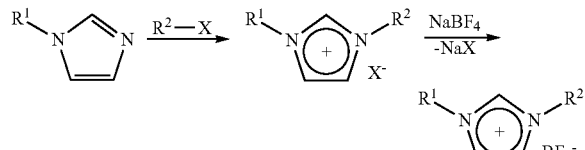

$R^1$ = methyl, vinyl, allyl
$R^2$ = ethyl, propyl, butyl, isobutyl, propargyl, allyl, crotyl, methallyl
X = Cl, Br The organic cation can comprise a linear, branched, or cyclic heteroalkyl unit, as described in US 2010/0174111. The term "heteroalkyl" refers to a cation comprising one or more heteroatoms chosen from nitrogen, oxygen, sulfur, boron, arsenic, boron, antimony, aluminum, or phosphorous capable of forming a cation. The heteroatom can be a part of a ring formed with one or more other heteroatoms, for example, pyridinyl, or imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, quinoxalines, alkyl phosphonium, and combinations thereof.

The anionic portion of the ionic liquid can comprise an inorganic, organic, or organometallic moiety, as described in US 2010/0174111. Non-limiting examples of anions include inorganic anions: halides, (e.g., anions of F, Cl, Br, and I); borides, $BX_4$, wherein X represents halogen, (e.g., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; tetrafluoroborates; tosylates; imides; $CO_3^{2-}$; $NO_2^{1-}$, $NO_3^{1-}$, $SO_4^{2-}$, $PO_4^{3-}$, $(CF_3)SO_3^{1-}$, and the like.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R)_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In some embodiments, suitable ionic liquids include, but are not limited to pyrrolidinium ionic liquids, imidiazolium ionic liquids, pyridinium ionic liquids, and phosphonium ionic liquids. In some embodiments, the ionic liquid comprises an anion selected from imides, acetates, halides, such as bromides and chlorides, tetrafluoroborates, phosphates, sulfates, and tosylates. The ionic liquid may comprise one or more of 1-butyl-1-methylpyrrolidinium-bis(trifluoromethylsulfonyl)imide, 1-butyl-3-methyl imidazolium acetate, 1-butyl-3-methyl imidazolium bromide, 1-butyl-4-methylpyridinium tetrafluoroborate, tributylethyl phosphonium diethylphosphate, tributylhexyl phosphonium bromide, tributylmethyl phosphonium chloride, tributylmethyl phosphonium dimethyl phosphate, tributylmethyl phosphonium methylsulfate, tributyloctyl phosphonium chloride, trihexylmethyl phosphonium tosylate, trihexyltetradecyl phosphonium bromide, trihexyltetradecyl phosphonium chloride.

The ionic liquid can be provided, or it can be generated in situ from appropriate precursors, or both. If it is generated in situ, the solvent comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates.

Optionally, an ionic solid, such as ammonium acetate (NH4OAc) and/or ammonium bromide (NH4Br), can be added to the mixture. Alternatively, a material which is capable of forming an ionic salt in solution can be added. The material can form the ionic salt in solution by combining with ions present in the solution. For example, in a solution containing bromide (for example in the form of HBr) or acetate ions (for example, in the form of acetic acid), ammonia could combine with the bromide or acetate ions forming ammonium bromide or ammonium acetate. In some embodiments, the use of one or more ionic solids or materials capable of forming an ionic salt in solution provided an additional reduction in the level of impurities.

The solvent can optionally include an aqueous solvent, such as water, if desired.

In an embodiment, the amount of ionic solid and/or material capable of forming an ionic salt in solution ranges up to about 75 wt % relative to the weight of the solvent, or from about 5 wt % to about 75 wt %, relative to the weight of the solvent, or from about 10 wt % to about 40 wt %, relative to the weight of the solvent. The solvent includes the ionic liquid and/or ionic liquid precursors, the optional ionic solid or material capable of forming an ionic salt in solution, and the optional aqueous solvent.

In one embodiment, the invention can be combined with other purification steps, if desired. Such additional processing steps have been described in the general literature and are well known to those of ordinary skill in the art to be used in various combinations to purify oxidation products of the invention. See for example, the references cited in this application and the art cited therein.

EXAMPLE 1

In this experiment, the ionic liquid was contacted with a physical mixture of terephthalic acid and 4-CBA. Commercial terephthalic acid and 4-CBA (>98% purity obtained from Aldrich) were purchased and mixed (1.990 g purified terephthalic acid and 0.01 g. 4-CBA) to obtain 5000 wppm 4-CBA. The physical mixture was contacted with various ionic liquids at 100° C. for 2 hrs. After cooling to room temperature, the ionic liquid phase was removed, leaving a solid. The solid material was washed with water and dried overnight at 100° C. The solid was then analyzed and compared to the starting ratio.

Two phosphonium ionic liquids were found to completely solubilize the 4-CBA/terephthalic acid mixture at 100° C. when contacted at a 1:1 mol ratio of solids to ionic liquid: tributyl(ethyl)phosphonium diethylphosphate and tributyl (methyl)phosphonium dimethyl phosphate. When tributyl (methyl)phosphonium dimethyl phosphate was contacted with 4-CBA alone under similar conditions, a clear solution ensued. When tributyl(methyl)phosphonium dimethyl phosphate was contacted with terephthalic acid alone at 100° C., only about 36% of the solid was soluble in the ionic liquid. Thus, although both components are soluble in the ionic liquid, 4-CBA appears to have greater solubility, and when the moles of solid exceed the moles of ionic liquid, not all of the solid is soluble.

Six ionic liquids were shown to remove more than 80% of the 4-CBA. Table 1 shows the results:

| Removal of 4-CBA from a Physical Mixture with TA | | | |
|---|---|---|---|
| Description | % removal of 4CBA | Wt ratio IL/solid | Mol ratio IL/solid |
| 0.01 g 4-CBA and 1.990 g PTA, 5000 ppm 4-CBA | 11 | — | — |
| Acetic Acid | 10 | 1.42 | NA* |
| 1-Butyl-1-methylpyrrolidinium-bis(trifluoromethylsulfonyl)imide | 93 | 3.85 | 1.49 |
| 1-Butyl-3-methyl imidazolium acetate | 90 | 1.78 | 1.49 |
| 1-Butyl-3-methyl imidazolium bromide | 55 | 2.32 | 1.75 |
| 1-Butyl-4-methyl pyridinium tetrafluoroborate | 77 | 2.32 | 1.61 |
| Tributylethyl phosphonium diethylphosphate | 74 | 2.33 | 1.01 |
| Tributylhexyl phosphonium bromide | 72 | 2.27 | 1.02 |
| Tributylmethyl phosphonium chloride | 69 | 2.04 | 1.33 |
| Tributylmethyl phosphonium dimethylphosphate | 80 | 2.07 | 1.00 |
| Tributylmethyl phosphonium methylsulfate | 72 | 1.96 | 0.99 |
| Tributyloctyl phosphonium chloride | 74 | 2.06 | 0.97 |
| Trihexylmethyl phosphonium tosylate | 61 | 2.84 | 1.00 |
| Trihexyltetradecyl phosphonium bromide (Cyphos 102) | 99 | 3.33 | 0.98 |
| Trihexyltetradecyl phosphonium chloride (Cyphos 101) | 97 | 5.00 | 1.51 |

Reaction time was 2 hours at 100 C. After cooling to room temperature, the solid was separated from the IL and washed with water and dried at 100 C. prior to LC analysis.
*Mol ratio acetic acid/mol solid = 4.00

EXAMPLE 2

In this experiment, physical mixtures of terephthalic acid and 4-CBA were contacted with two or more ionic liquids, ionic liquids with ionic solids, and ionic liquids and water using the procedure discussed above. The results are shown in Table 2:

| Removal of 4-CBA from a Physical Mixture with TA Using a Combination of ILs, ILs and Ionic Solids, and ILs with water | | | |
|---|---|---|---|
| Description | % removal of 4CBA | wt ratio IL/solid | mol ratio IL/solid |
| 1-Butyl-1-methylpyrrolidinium-bis(trifluoromethylsulfonyl)imide + 22% water | 80 | 3.70 | 1.40 |
| 1-Butyl-1-methylpyrrolidinium-bis(trifluoromethylsulfonyl) imide + 1-Butyl-3-methyl imidazolium acetate | 86 | 1.72 | 1.07 |
| 1-Butyl-1-methylpyrrolidinium-bis(trifluoromethylsulfonyl)imide + Trihexyltetradecyl phosphonium bromide (Cyphos 102) | 86 | 3.05 | 0.98 |
| 1-Butyl-3-methyl imidazolium acetate + 1-Butyl-3-methyl imidazolium bromide | 48 | 1.29 | 1.03 |
| 1-Butyl-methyl imidazolium acetate + 35% wt water | 44 | 1.22 | 1.02 |
| 1-Butyl-3-methyl imidazolium acetate + Trihexyltetradecyl phosphonium bromide (Cyphon 102) | 93 | 2.58 | 0.98 |
| Ammonium acetate + 1-Butyl-3-methyl imidazolium acetate + | 70 | 1.54 | 1.80 |

-continued

Removal of 4-CBA from a Physical Mixture
with TA Using a Combination of ILs, ILs
and Ionic Solids, and ILs with water

| Description | % removal of 4CBA | wt ratio IL/solid | mol ratio IL/solid |
|---|---|---|---|
| 1-Butyl-3-methyl imidazolium bromide Ammonium acetate + Ammonium bromide + 1-Butyl-3-methyl imidazolium bromide | 42 | 0.79 | 1.00 |
| Ammonium bromide + 1-Butyl-3-methyl imidazolium bromide | 58 | 0.95 | 1.01 |
| Ammonium bromide + 66% wt water | 71 | 0.59 | 1.00 |

EXAMPLE 3

In this experiment, crude terephthalic acid was obtained and analyzed for 4-CBA level.

Crude terephthalic acid containing 3190 wppm of 4-CBA was generated from the oxidation of xylenes in the presence of acetic acid and ionic liquid.

A second sample of crude terephthalic acid containing 429 wppm of 4-CBA was generated from the oxidation of xylenes in the presence of acetic acid and ionic liquid.

A third sample of crude terephthalic acid containing 9847 wppm of 4-CBA was generated from the oxidation of xylenes in the presence of acetic acid and ionic liquid.

Each of the crude terephthalic acid samples was contacted with various ionic liquids at 100° C. for 2 hrs. After cooling to room temperature, the ionic liquid phase was removed, leaving a solid. The solid material was washed with water and dried overnight at 100° C. The solid was then analyzed and compared to the initial amount.

The crude terephthalic acid co-crystallizes with the 4-CBA so that the 4-CBA crystals are embedded in the crystals of terephthalic acid. The results showed removal of up to 87% of the 4-CBA. Table 3 shows the results:

Removal of 4-CBA from Crude TA

| Liquid | % removal of 4CBA | wt ratio IL/solid | mol ratio IL/solid |
|---|---|---|---|
| 1-Butyl-3-methyl imidazolium acetate | 82 | 1.21 | 1.01 |
| 1-Butyl-1-methylpyrrolidinium-bis (trifluoromethylsulfonyl)imide | 30 | 1.28 | 0.50 |
| Trihexyltetradecyl phosphonium chloride (Cyphos 101) | 36 | 1.64 | 0.50 |
| Trihexyltetradecyl phosphonium bromide (Cyphos 102) | 48 | 1.74 | 0.51 |
| 1-Butyl-3-methyl imidazolium acetate | 83 | 1.20 | 1.00 |
| 1-Butyl-1-methylpyrrolidinium-bis (trifluoromethylsulfonyl)imide | 65 | 1.28 | 0.50 |
| Trihexyltetradecyl phosphonium chloride (Cyphos 101) | 77 | 1.61 | 0.51 |
| Trihexyltetradecyl phosphonium bromide (Cyphos 102) | 87 | 1.73 | 0.51 |
| 1-Butyl-1-methylpyrrolidinium-bis (trifluoromethylsulfonyl)imide | 35 | 3.82 | 1.50 |
| Trihexyltetradecyl phosphonium chloride (Cyphos 101) | 60 | 4.94 | 1.51 |
| Trihexyltetradecyl phosphonium bromide (Cyphos 102) | 27 | 5.11 | 1.50 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A process for purifying crude or contaminated terephthalic acid comprising:
   contacting the crude or contaminated terephthalic acid with a solvent in the absence of an oxidizing agent to form a purified product having at least 30 wt % less 4-carboxybenzaldehyde compared to the crude or contaminated terephthalic acid, wherein the solvent consists essentially of an ionic liquid, optionally an ionic solid or a material capable of forming an ionic salt, and optionally an aqueous solvent;
   separating the purified product from the solvent, and
   wherein the ionic liquid is formed in situ from at least one ionic liquid precursor.

2. The process of claim 1, further comprising:
   heating the solvent before contacting the crude or contaminated terephthalic acid with the solvent.

3. The process of claim 1 wherein the solvent is at a temperature in a range of about 50° C. to about 250° C.

4. The process of claim 1, further comprising:
   contacting the purified product with a second solvent in the absence of an oxidizing agent, the second solvent consisting essentially of an ionic liquid, optionally an ionic solid or a material capable of forming an ionic salt in the absence of an oxidizing agent, and optionally an aqueous solvent.

5. The process of claim 1, further comprising recovering the purified product.

6. The process of claim 1, wherein the purified product has at least 50 wt % less 4-carboxybenzaldehyde compared to the crude or contaminated terephthalic acid.

7. The process of claim 1, wherein the purified product contains less than about 2500 ppm of 4-carboxybenzaldehyde.

8. The process of claim 1, wherein the purified product contains less than about 500 ppm of 4-carboxybenzaldehyde.

9. The process of claim 1, wherein a cation of the ionic liquid is formed from imidazoles, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, quinoxalines, alkyl phosphonium, or combinations thereof.

10. The process of claim 1, wherein an anion of the ionic liquid is halides, borides, phosphates, arsenates, stibates, acetate, carboxylates, azolates, sulfates, tetrafluoroborates, tosylates, imides, acyl units, $CO_3^{2-}$, $NO_2^{1-}$, $NO_3^{1-}$, $SO_4^{2-}$, $PO_4^{3-}$, $(CF_3)SO_3^{1-}$, derivatives thereof, or combinations thereof.

11. The process of claim 1, wherein there are at least two ionic liquids.

12. The process of claim 1, further comprising washing the purified product with water to remove the solvent.

13. The process of claim 1, wherein the solvent includes the ionic solid or a material capable of forming an ionic salt.

14. The process of claim 1, wherein the solvent includes the ionic solid, and wherein the ionic solid is ammonium acetate or ammonium bromide.

15. The process of claim 1, wherein the solvent includes the aqueous solvent, and wherein the aqueous solvent is water.

16. A process for purifying crude or contaminated terephthalic acid comprising:
    contacting the crude or contaminated terephthalic acid with a solvent in the absence of an oxidizing agent to form a purified product having at least 60 wt % less 4-carboxybenzaldehyde compared to the crude or contaminated terephthalic acid, wherein the solvent consists essentially of an ionic liquid, optionally an ionic solid or a material capable of forming an ionic salt, and optionally an aqueous solvent, and wherein the solvent is at a temperature in a range of about 50° C. to about 200° C.;
    separating the purified product from the solvent;
    recovering the purified product, and
    wherein the ionic liquid is formed in situ from at least one ionic liquid precursor.

17. The process of claim 16, wherein a cation of the ionic liquid is formed from imidazoles, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, quinoxalines, alkyl phosphonium, or combinations thereof.

18. The process of claim 16, wherein an anion of the ionic liquid is halides, borides, phosphates, arsenates, stibates, acetate, carboxylates, azolates, sulfates, tetrafluoroborates, tosylates, imides, acyl units, $CO_3^{2-}$, $NO_2^{1-}$, $NO_3^{1-}$, $SO_4^{2-}$, $PO_4^{3-}$, $(CF_3)SO_3^{1-}$, derivatives thereof, or combinations thereof.

19. The process of claim 16, wherein the solvent includes the ionic solid and wherein the ionic solid is ammonium acetate or ammonium bromide.

* * * * *